US00PP29437P2

(12) United States Plant Patent
Brazelton et al.

(10) Patent No.: US PP29,437 P2
(45) Date of Patent: Jul. 3, 2018

(54) BLUEBERRY PLANT NAMED 'ZF06-051'

(50) Latin Name: ***Vaccinium corymbosum* hybrid**
Varietal Denomination: ZF06-051

(71) Applicant: THE CONARD-PYLE COMPANY, West Grove, PA (US)

(72) Inventors: David M. Brazelton, Walterville, OR (US); Adam L. Wagner, Eugene, OR (US); Peter S. Boches, Hilo, HI (US); Antonio A. Alamo Bermudo, Sevilla (ES)

(73) Assignee: THE CONRAD-PYLE COMPANY, West Grove, PA (US)

( * ) Notice: Subject to any disclaimer, the term of this patent is extended or adjusted under 35 U.S.C. 154(b) by 0 days.

(21) Appl. No.: 15/731,304

(22) Filed: May 23, 2017

(51) Int. Cl.
*A01H 5/08* (2018.01)

(52) U.S. Cl.
USPC ..... Plt./157

(58) Field of Classification Search
USPC ..... Plt./157
See application file for complete search history.

*Primary Examiner* — Annette H Para
(74) *Attorney, Agent, or Firm* — Buchanan Ingersoll & Rooney PC

(57) ABSTRACT

A new and distinct blueberry plant variety, herein referred to by its cultivar name 'ZF06-051', is provided. The variety is produced from a cross of 'Gulfcoast' and 'Cape Fear'. The new variety is an attractive shape which is round, compact, and hedge-like and forms dark green leaves and medium sized fruit. The flowers produced are cylindrical to campanulate with moderate amounts of pink anthocyanin before they fully open. The new variety is a low chill ornamental variety and is well suited for nursery, landscape, and home garden use.

4 Drawing Sheets

Latin name of the family, genus, and species:
Family—Ericaceae.
Genus—*Vaccinium.*
Species—*corymbosum* hybrid.
Variety denomination: The new blueberry plant claimed is of the variety denominated 'ZF06-051'.

CROSS REFERENCE TO RELATED APPLICATIONS

This applications claims priority to U.S. Provisional Application 62/392,196 filed on May 23, 2016; of which the content of is hereby expressly incorporated by reference in its entirety for all purposes and is assigned to the assignee hereof.

STATEMENT REGARDING FEDERALLY-SPONSORED RESEARCH AND DEVELOPMENT

None.

BACKGROUND OF THE INVENTION

'ZF06-051' was selected from a seedling family in Lowell, Oreg. in 2006 for its attractive shape and foliage. The selection was propagated by softwood cuttings in 2006 using traditional methods and a replicated plot of 3 plants was established in the same location in 2007. The variety has been observed in this location in 2008 through 2012. It has also been observed in California and Washington in 2011 and 2012.

SUMMARY OF THE INVENTION

Pedigree and History: The new blueberry plant originated from a cross of 'Gulfcoast' (female parent, unpatented) by 'Cape Fear' (pollen parent, unpatented) in 1987 in Beltsville, Md.

The seedling family that produced 'ZF06-051' was initially grown in 50 cell propagation trays and planted into a high density seedling nursery in 2004. The new blueberry plant variety 'ZF06-051' was propagated by softwood cuttings in 2006 using traditional methods and a replicated plot of 3 plants was established in Lowell, Oreg. in 2007. Starting from these plants, 'ZF06-051' has been propagated annually with no changes in the appearance of the plant or expression of its unique traits. Plants derived from these were successfully used to establish in vitro culture lines in 2010 and 2011. The variety has been observed in Lowell, Oreg. from 2008 through 2012. It has also been observed in California and Washington in 2011 and 2012. Plants of 'ZF06-051' propagated from softwood cuttings or in vitro are phenotypically stable and exhibit the same characteristics as the original plant.

After being selected in 2006 and propagated successfully, in 2009 plants of 'ZF06-051' were sent to field trial locations near Oxnard, Calif.; Lynden, Wash.; Paterson, Wash.; and Delano, Calif. In 2013, plants were sent to trials at commercial nursery locations in California, Georgia, Oregon, and Louisiana; as well as a field trial location in Tala, state of Jalisco, Mexico. 'ZF06-051' did not consistently fruit at colder locations in Washington but was well adapted and fruited well at warmer trial locations in California, Georgia, and Louisiana. In the subtropical climate of Jalisco, Mexico, 'ZF06-051' did not fruit well. Thus, 'ZF06-051' does not consistently fruit at colder trial site locations in zones 7 and higher, but is well adapted to low chill climates in zones 8-10.

The new blueberry plant 'ZF06-051' as it grows in Lowell, Oreg. and Delano, Calif. is distinguished by dark green, elliptical-shaped leaves. The plant shape is compact and rounded, growing to height of two to four feet tall at maturity. Flushes of new growth have a reddish tinge. The flowers are cylindrical to campanulate with moderate amounts of pink anthocyanin before they fully open. The fruit is medium to small and abundant, with moderate amounts of bloom, a small calyx end depression and a sweet taste. Due to its compact growth habit, attractive foliage and flowers, and adaptation to lower chill climates, 'ZF06-051' makes an excellent container or specimen plant in low chill growing areas.

The new variety can be readily distinguished from its ancestors. The parents 'Gulf Coast' and 'Cape Fear' were not evaluated in the same environment as 'ZF06-051' but some comparisons can be made based on published descriptions. In comparison to 'Gulfcoast' which has vigor and plant size typical of a commercial southern highbush blueberry, 'ZF06-051' is less vigorous and smaller in stature. Fruit and leaves of 'ZF06-051' are similar in shape to 'Gulfcoast'. In comparison to 'Cape Fear', 'ZF06-051' is less vigorous and smaller in stature and 'Cape Fear' has much larger fruit. The new variety can also be readily distinguished from other cultivars. For example, ZF06-051 differs from ornamental variety 'Sunshine Blue' in that 'ZF06-051' has a more compact growing habit and has leaves that are darker in color. 'ZF06-051' is similar to the ornamental variety 'Top Hat' in its size and shape, but has leaves that are darker in color and has a lower chilling requirement.

As detailed above, the new variety has been found to undergo asexual propagation by a number of routes. Asexual propagation has shown that the characteristics of the new variety are stable and strictly transmissible by such asexual propagation from one generation to another. Accordingly, the new variety undergoes asexual propagation in a true-to-type manner.

The new variety has been named 'ZF06-051'.

BRIEF DESCRIPTION OF THE DRAWINGS

The accompanying photographs show, as nearly true as it is reasonable possible to make the same in color illustrations of this character, typical specimens of the new variety.

DETAILED BOTANICAL DESCRIPTION

Figure 1:
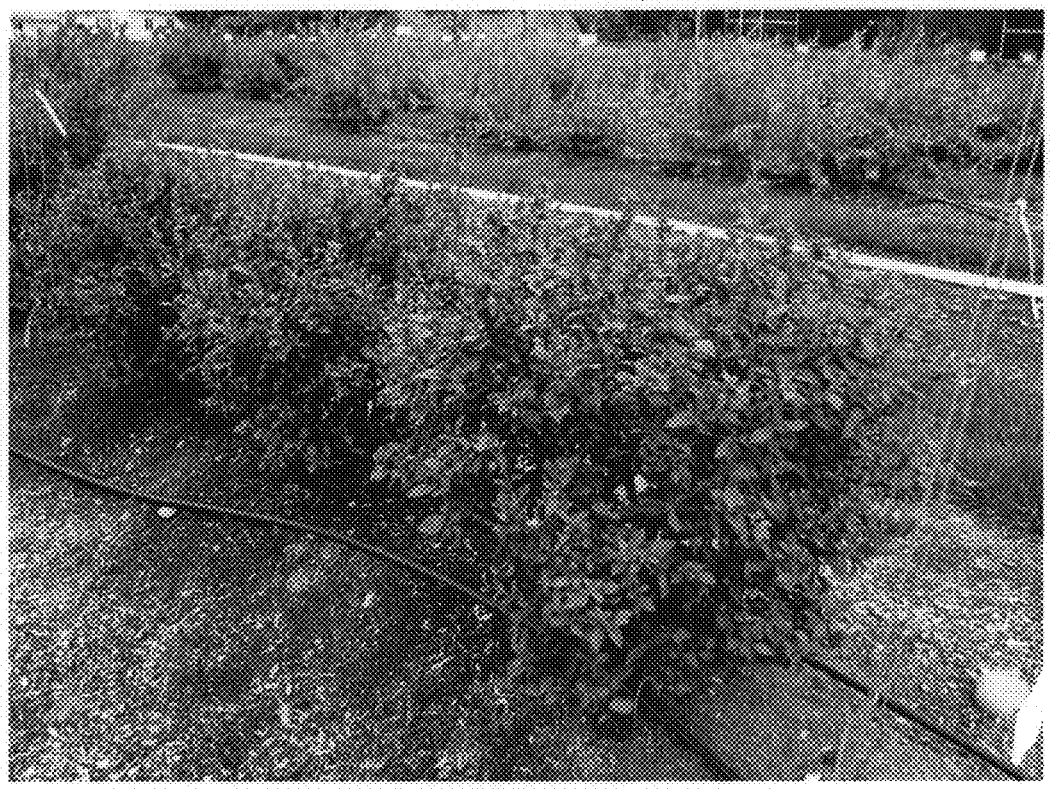
FIG. 1—illustrates a specimen of the plant.
Figure 2:
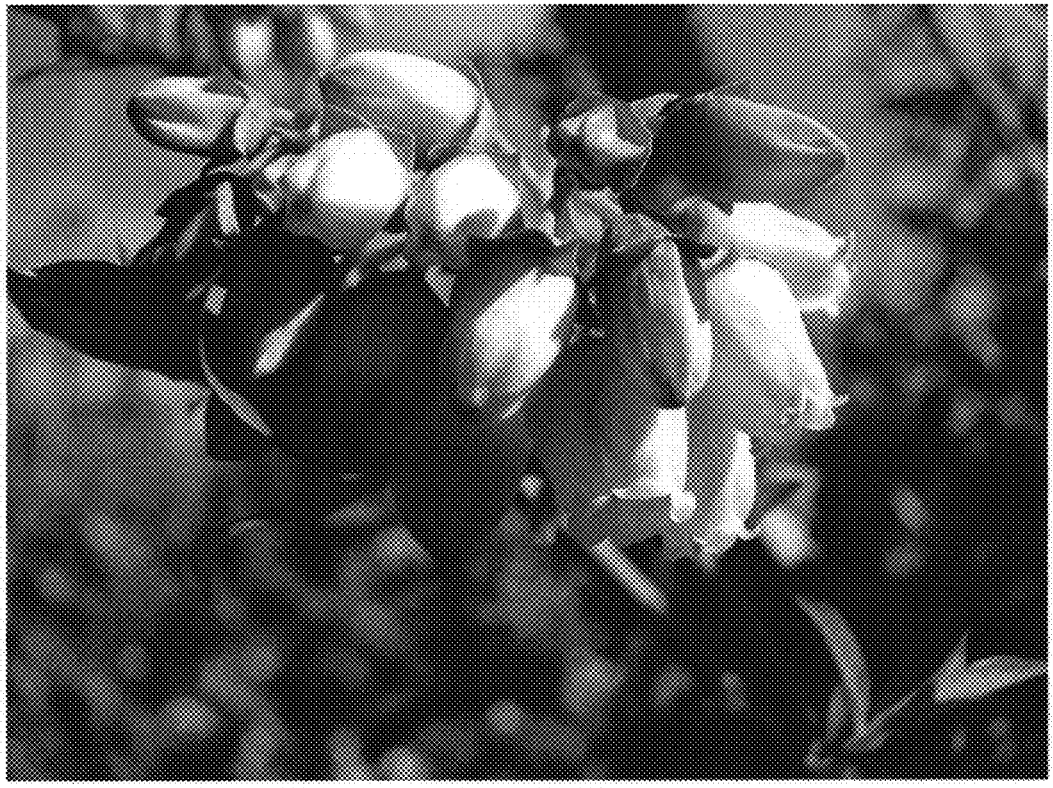
FIG. 2—illustrates a specimen of the inflorescence.
Figure 3:
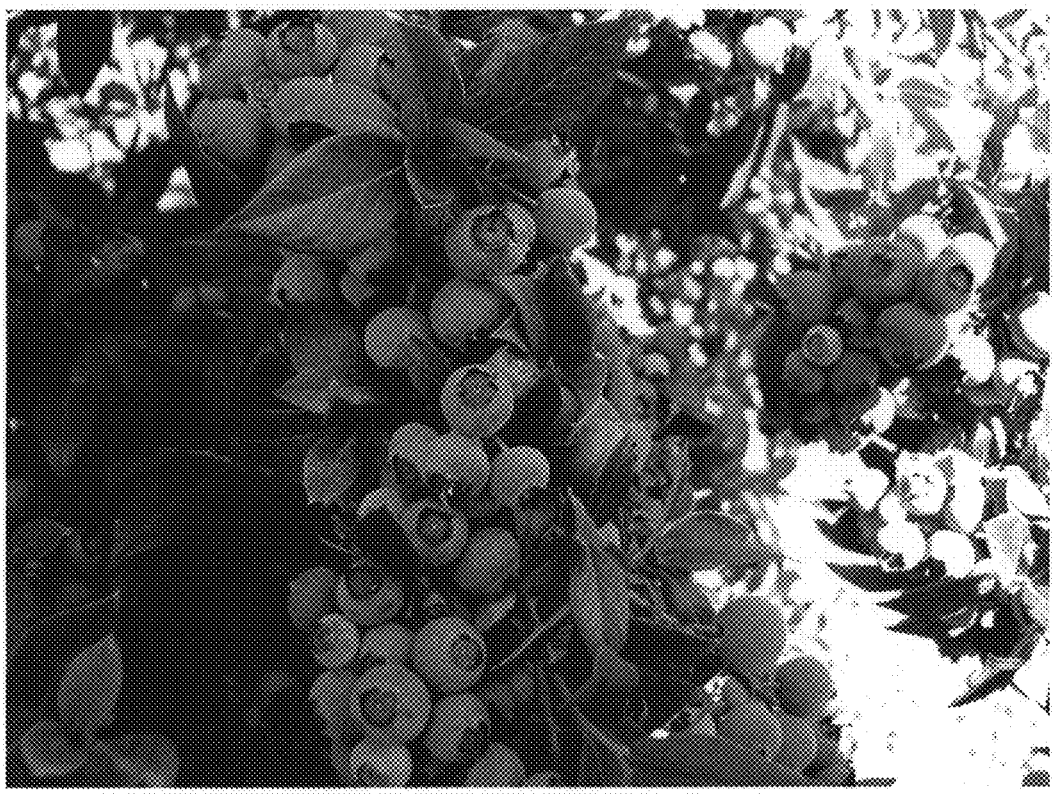
FIG. 3—illustrates specimens of the fruit.
Figure 4:
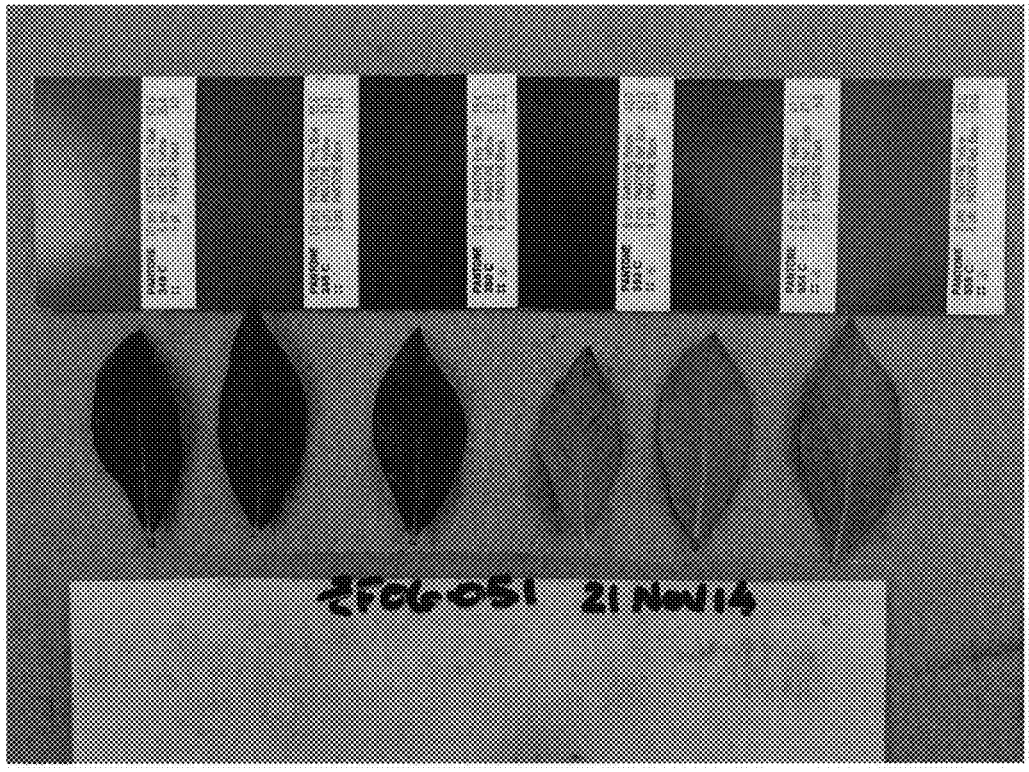
FIG. 4—illustrates specimens of the leaf in plan view, obverse and reverse.

The following detailed description sets forth the distinctive characteristics of 'ZF06-051'. The data which defines these characteristics was collected from asexual reproductions of the original selection. Dimensions, sizes, colors, and other characteristics are approximations and averages set forth as accurately as possible. The descriptions relate to plants grown in the field in Lowell, Oreg., USA. Color designations are from "The Pantone Book of Color" (by Leatrice Eiseman and Lawrence Herbery, Harry N. Abrams, Inc., Publishers, New York 1990). Where the Pantone color designations differ from the colors in the photographs, the Pantone colors are accurate.

PLANT

General:

a. *Plant height*.—Approximately 21 inches on average in typical four-year-old specimens.

b. *Canopy diameter*.—Approximately 23 inches on average in typical four-year-old specimens.

c. *Growth habit*.—Round with upright shoots, short stature.

d. *Plant vigor*.—Vigorous.

e. *Twigginess*.—Moderately twiggy.

f. *Evergreeness*.—Semi evergreen in Lowell, Oreg.

g. *Cold hardiness*.—Based on pedigree, estimated USDA hardiness zones 8-10.

h. *Chilling requirement*.—Based on pedigree, approximately 300 hours.

i. *Productivity*.—In Lowell, Oreg., average per plant harvest weight on four-year-old plants is approximately 2.5 lbs.

j. *Propagation*.—Easy to propagate from softwood cuttings.

k. *Resistance/susceptibility to root rot* (*phytopthora cinnamomii*).—Does not appear to be overly susceptible.

l. *Resistance/susceptibility to stem blight* (*botryosphaeria* sp).—Undetermined.

m. *Resistance/susceptibility to phomopsis twig blight* (*phomopsis vaccinii*).—Does not appear to be overly susceptible.

n. *Resistance/susceptibility to botryosphaeria stem canker* (*botryosphaeria corticis*).—Undetermined.

o. *Resistance/susceptibility to bacterial cane canker* (*pseudomonas syringae*).—Does not appear to be overly susceptible.

p. *Resistance/susceptibility to botrytis blight* (*botrytis cinerea*).—Does not appear to be overly susceptible.

q. *Resistance/susceptibility to leaf spot* (*septoria* spp.).—Does not appear to be overly susceptible.

r. *Resistance/susceptibility to leaf rust* (*naohidemyces vaccinii*).—Does not appear to be overly susceptible.

s. *Resistance/susceptibility to bud mites* (*acalatus vaccinii*).—Undetermined.

t. *Survival*.—Good.

u. *Suckering tendency*.—Low.

STEM

General:

a. *Surface texture of new wood*.—Smooth.

b. *Surface texture of one-year-old wood*.—Smooth.

c. *Surface texture of three-year-old wood*.—Rough.

d. *Color of new wood*.—Commonly near Green Olive 17-0535.

e. *Color of rough bark of one-year-old*.—Commonly near Green Oasis 15-0538 and Cinnabar 18-1540.

f. *Color of rough bark of three-year-old*.—Commonly near Antelope 16-1126 and Grey Sand 13-1010.

g. *Internode length*.—Approximately 5.55 mm on average.

FOLIAGE

General:

a. *Leaf color upper leaf surface*.—Mature leaves are commonly near Thyme 19-0309 and Black Forest 19-0315 and new leaves are commonly near Rose wine 17-1623 and Peridot 17-0336.
b. *Leaf color lower leaf surface*.—Commonly near Watercress 17-0220.
c. *Leaf shape*.—Elliptical, with acute apex and base.
d. *Leaf margins*.—Entire.
e. *Leaf length*.—Approximately 40.49 mm on average.
f. *Leaf width*.—Approximately 15.22 mm on average.
g. *Pubescence of upper leaf surface*.—Absent.
h. *Pubescence of lower leaf surface*.—Absent.
i. *Pubescence leaf margins*.—Absent.

Petioles:

a. *Length*.—Approximately 1.77 mm on average.
b. *Color*.—Commonly near Sweet Pea 15-0531.
c. *Surface texture*.—Smooth.

INFLORESCENCE

General:

a. *Leafing vs. flowering*.—Flower bud break occurs prior to vegetative bud break in Lowell, Oreg. Flowers persist through initial vegetative growth period.
b. *Flower arrangement*.—Clusters arranged alternately along branches.
c. *Flower shape*.—Cylindrical.
d. *Flower fragrance*.—Faint, sweet
e. *Immature flower color*.—Commonly near Pastel Parchment 11-0603 and Holly Berry 17-1633.
f. *Pollen staining*.—Staining with 2% acetocarmine: 95%.
g. *Self-compatibility*.—Moderate; approximately 46% of self-pollinated flowers reach maturity on average.
h. *Flower length*.—Approximately 8.33 mm on average.
i. *Flowering period*.—In Lowell, Oreg., flowers from late March through mid to late May.
j. *Length of peduncle*.—Variable, approximately 14.84 mm on average.
k. *Color of peduncle*.—Approximately near Mellow Green 12-0426.
l. *Length of pedicle*.—Approximately 3.14 mm on average.
m. *Color of pedicle*.—Commonly near Mellow Green 12-0426.
n. *Number of flowers*.—Commonly 5 or 6.
o. *Flower cluster density*.—Loose.

Corolla:

a. *Color*.—Commonly near Antique White 11-0602.
b. *Length*.—Approximately 6.3 mm on average.
c. *Diameter*.—Approximately 4.39 mm on average.
d. *Aperture*.—Approximately 4.1 mm on average.
e. *Stigma location*.—Variable, from about 0.3 mm above the lip of corolla to even with lip of corolla.
f. *Texture*.—Smooth.

Calyx:

a. *Diameter*.—Approximately 6.9 mm on average.
b. *Color*.—Commonly near Green Olive 17-0535 and Spinach Green 16-0439.
c. *Calyx surface*.—Smooth.

Pistil:

a. *Color*.—Commonly near Green Oasis 15-0538.
b. *Style*.—Length — approximately 6.15 mm on average.

Anther:

a. *Length*.—Approximately 3.9 mm on average.
b. *Color*.—Commonly near Burnt Orange 16-1448.

Pollen:

a. *Abundance*.—Medium.
b. *Color*.—Commonly near Pale Banana 12-0824.

FRUIT

General:

a. *Time of fruit ripening*.—Fruit typically begins ripening in early to mid-July, with 50% ripe typically occurring in late July and 95% typically in early August.
b. *Berry cluster*.—Loose.
c. *Berries per cluster*.—Commonly 5 or 6.
d. *Immature berry color*.—Commonly near Herbal garden 15-0336 and Damson 18-1716.
e. *Berry skin color on plant*.—Commonly near Dapple Grey 16-3907.
f. *Berry skin color after harvest*.—Commonly near Dapple Grey and Patriot Blue 19-3925.
g. *Berry skin color after polishing*.—Commonly near Dark Navy 19-4013.
h. *Berry surface wax abundance*.—Moderate wax and moderately persistent.
i. *Berry flesh color*.—Commonly near Winter White 11-0507.
j. *Berry weight*.—Approximately 0.99 g on average
k. *Berry height*.—Approximately 9.5 mm on average.
l. *Berry diameter*.—Approximately 11.85 mm on average.
m. *Calyx aperture*.—Approximately 4.6 mm on average.
n. *Calyx lobes*.—Indistinct.
o. *Calyx depth*.—Approximately 0.76 mm on average.
p. *Pedicel length*.—Approximately 5.7 mm on average.
q. *Pedicel surface texture*.—Smooth.
r. *Peduncle length*.—Approximately 8.87 mm on average.
s. *Peduncle surface texture*.—Smooth.
t. *Berry detachment force*.—Medium.
u. *Berry shape*.—Spherical.
v. *Pedicel scar*.—Dry and moderately small; approximately 2.9 mm on average in diameter.
w. *Berry flavor*.—Mild, sweet.
x. *Berry texture*.—Mealy.
y. *Firmness*.—Moderately firm.

SEED

General:

a. *Quantity of seeds per berry*.—14 on average.
b. *Seed color*.—Commonly near Glazed Ginger 18-1154.
c. *Seed weight*.—Approximately 0.5 mg on average.
d. *Seed length*.—Approximately 1.86 mm on average.
e. *Seed width*.—Approximately 1.32 mm on average.

The new 'ZF06-051' variety has not been observed under all possible environmental conditions to date. Accordingly, it is possible that the phenotypic expression may vary somewhat with changes in temperature, light intensity and duration, cultural practices, and other environmental conditions.

The invention claimed is:

1. A new and distinct blueberry plant characterized by the following combination of characteristics:

(a) displays a compact and rounded plant, (b) provides attractive foliage with dark green, elliptical leaves, (c) shows cylindrical to campanulate flowers of moderate pink anthocyanin coloration before they fully open;

(d) provides medium to small fruit which is abundant and sweet, and (e) is adapted for lower chill climates, substantially as herein shown and described.

* * * * *